United States Patent [19]

Kwiatkowski et al.

[11] Patent Number: 4,986,934

[45] Date of Patent: Jan. 22, 1991

[54] PHOTOCHROMIC COMPOUND AND ARTICLES CONTAINING THE SAME

[75] Inventors: Patricia L. Kwiatkowski, Akron; David B. Knowles, Wadsworth, both of Ohio

[73] Assignee: PPG Industries, Inc., Pittsburgh, Pa.

[21] Appl. No.: 288,051

[22] Filed: Dec. 21, 1988

Related U.S. Application Data

[63] Continuation of Ser. No. 173,229, Mar. 25, 1988, abandoned.

[51] Int. Cl.$^5$ .................... G02B 5/23; C07D 498/20
[52] U.S. Cl. ............................ 252/586; 351/163; 544/70; 544/71; 350/354; 252/582
[58] Field of Search ................. 252/582, 586; 544/70, 544/71; 350/354; 351/163; 430/345

[56] References Cited

U.S. PATENT DOCUMENTS

| | | | |
|---|---|---|---|
| 3,562,172 | 2/1971 | Ono et al. | 252/300 |
| 3,578,602 | 5/1971 | Ono et al. | 252/300 |
| 3,923,524 | 12/1975 | Haase | 96/140 |
| 4,215,010 | 7/1980 | Hovey et al. | 252/300 |
| 4,342,668 | 8/1982 | Hovey et al. | 252/586 |
| 4,634,767 | 1/1987 | Hoelscher et al. | 544/71 |
| 4,637,698 | 1/1987 | Kwak et al. | 351/163 |
| 4,719,296 | 6/1988 | Irie et al. | 544/71 |
| 4,851,530 | 7/1989 | Rickwood | 544/71 |
| 4,889,413 | 12/1989 | Ormsby et al. | 350/354 |
| 4,913,544 | 4/1990 | Rickwood et al. | 252/586 X |

FOREIGN PATENT DOCUMENTS

| | | |
|---|---|---|
| 63-30486 | 2/1986 | Japan . |
| 62-155283 | 7/1987 | Japan . |
| 63-30487 | 2/1988 | Japan . |
| 63-30488 | 2/1988 | Japan . |
| 63-66186 | 3/1988 | Japan . |
| 2171404 | 8/1986 | United Kingdom . |
| 2174711A | 11/1986 | United Kingdom . |
| 2200908A | 8/1988 | United Kingdom .................. 544/71 |

OTHER PUBLICATIONS

Study of Photochromic Properties of Spirochromenes Produced from 4-Azaindoline by IR Spectra, M. T. Gugava et al; C. A. Selecto, Issue 15, 1987, Abstract 107:31062d.

Diazaindenes and Their Quaternary Salts, Part I, by G. E. Ficken et al; J. Chem. Soc., pp. 3202-3212, (1959).

Diazaindenes and Their Quaternary Salts, Part III, by G. E. Ficken et al, J. Chem. Soc., pp. 584–588, (1961).

*Primary Examiner*—Richard D. Lovering
*Assistant Examiner*—Daniel S. Metzmaier
*Attorney, Agent, or Firm*—Irwin M. Stein

[57] ABSTRACT

Described are spirobenzoxazine pyrrolo pyridine compounds. Also described is the use of such compounds as photochromic substances in organic host materials such as an organic transparent plastic material, e.g., an ophthalmic lens, to impart a photochromic response thereto.

26 Claims, No Drawings

PHOTOCHROMIC COMPOUND AND ARTICLES CONTAINING THE SAME

This is a continuation of application Ser. No. 173,229, filed Mar. 25, 1988, now abandoned.

DESCRIPTION OF THE INVENTION

The present invention relates to novel compounds and to compositions and articles containing such compounds. More particularly, the present invention relates to novel photochromic compounds and articles containing same. Photochromism is a reversible phenomenon illustrated by a compound which, when exposed to the radiation of light involving ultraviolet rays such as sunlight or the light of a mercury lamp, changes color and then returns to its original color if the radiation is discontinued or the compound is stored in the dark. A compound illustrating this property is called a "photochromic compound".

Various types of photochromic compounds have been synthesized and suggested for use in applications in which a color change or darkening is induced by sunlight. For example, spiro(indolino) naphthoxazine compounds are described in U.S. Pat. Nos. 3,562,172, 3,578,602, 4,215,010, and 4,342,668. Spiro(indolino) pyridobenzoxazines are described in U.S. Pat. No. 4,637,698. Such photochromic compounds either in crystalline form, in solution or dispersed in a transparent medium change rapidly from a colorless state to blue when exposed to sunlight or ultraviolet radiation. The compounds return to their original colorless state by being allowed to stand in the dark or by removing the source of strong ultraviolet radiation.

DETAILED DESCRIPTION OF THE INVENTION

In accordance with the present invention, there are provided novel spiro benzoxazine pyrrolo pyridine-type compounds represented by the following graphic formula I,

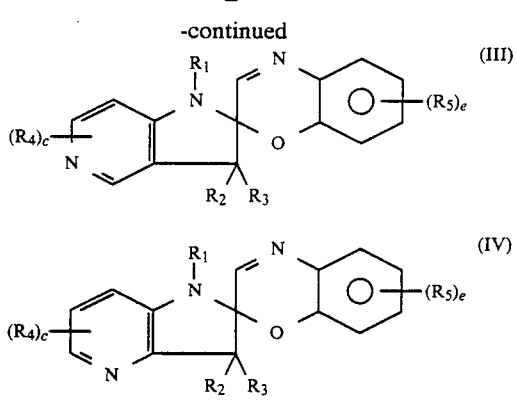

wherein ring B is a substituted or unsubstituted pyridine ring fused to the pyrrolo segment of the depicted molecule. The nitrogen hetero atom of the pyridine ring may be located at the 4', 5' or 7' positions of the molecule as illustrated in the following graphic formulae II-IV:

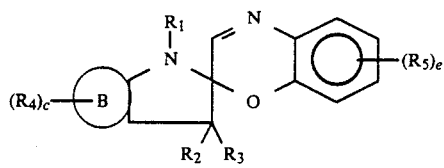

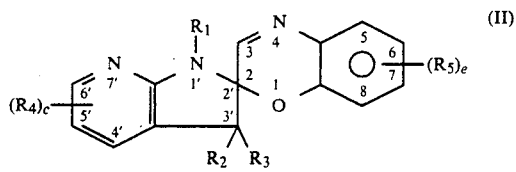

Graphic formula II depicts the numbering and orientation of the depicted molecule wherein the nitrogen hetero atom is located at the 7' position. The numbering in graphic formulae III and IV is the same as in graphic formula II. Formulae III and IV depict the molecule wherein the nitrogen hetero atom is located at the 5' and 4' positions respectively.

In the above graphic formulae I-IV, $R_1$ is selected from the group consisting of branched and straight chain $C_1$-$C_8$ alkyl, e.g., methyl, ethyl, propyl, butyl, etc., allyl, acrylyl($C_2$-$C_6$)alkyl. methacrylyl($C_2$-$C_6$)alkyl, carboxy e.g., β-carboxyethyl, γ-carboxypropyl and δ-carboxybutyl, cyano($C_2$-$C_6$)alkyl, e.g., β-cyanoethyl, γ-cyanopropyl, β-cyanoisopropyl, and δ-cyanobutyl, $C_1$-$C_4$ acyloxy($C_2$-$C_6$)alkyl, i.e., [$R_cC(O)OR_d$-, wherein $R_c$ is a $C_1$-$C_4$ alkyl and $R_d$ is a $C_2$-$C_6$ alkyl], e.g., acetoxyethyl, acetoxypropyl, propionyloxyethyl, acetoxybutyl, and propionyloxypropyl, hydroxy($C_2$-$C_6$)alkyl, e.g., hydroxyethyl, hydroxypropyl and hydroxybutyl, $(C_2H_4O)_m$·$CH_3$, wherein m is a number of from 1 to 6, and $C_1$-$C_3$ alkoxy($C_1$-$C_3$)alkyl, e.g., methoxymethyl, methoxyethyl, ethoxymethyl, ethoxyethyl, and methoxypropyl. Preferably, $R_1$ is selected from the group consisting of $C_1$-$C_4$ alkyl, carboxy($C_2$-$C_4$)alkyl, cyano($C_2$-$C_4$)alkyl, $C_1$-$C_4$acyloxy($C_2$-$C_4$)alkyl, e.g., $C_1$-$C_4$ acyloxyethyl, hydroxy($C_2$-$C_4$)alkyl. $(C_2H_4O)_m$·$CH_3$, wherein m is a number of from 1 to 3, e.g., 2, and $C_1$-$C_3$ alkoxy($C_1$-$C_3$)alkyl.

$R_2$ and $R_3$ are each selected from the group consisting of $C_1$-$C_5$ alkyl, phenyl, mono- and di-substituted phenyl, benzyl, or $R_2$ and $R_3$ may combine to form a cyclic ring selected from the group consisting of an alicyclic ring containing from 6 to 8 carbon atoms (including the spiro carbon atom), norbornyl and adamantyl. The aforesaid phenyl substituents may be selected from $C_1$-$C_4$ alkyl and $C_1$-$C_5$ alkoxy radicals. More particularly, $R_2$ and $R_3$ are each selected from $C_1$-$C_5$ alkyl, e.g., methyl, ethyl, propyl, butyl and pentyl, and phenyl. When one of $R_2$ or $R_3$ is a tertiary alkyl radical, such as tertiary butyl or tertiary amyl, the other is preferably an alkyl radical other than a tertiary alkyl radical.

$R_4$ in graphic formula I is selected from the group consisting of $C_1$-$C_5$ alkyl, halogen and $C_1$-$C_5$ alkoxy. While any halogen, i.e., chlorine, bromine, iodine and fluorine, may be used in respect to the aforesaid halogen, chlorine, fluorine and bromine, especially chlorine and fluorine are preferred. Preferably, $R_4$ is selected from 1 the group consisting of $C_1$-$C_2$ alkyl, chloro, fluoro and $C_1$-$C_2$ alkoxy.

The letter "c" in formula I is 0 or 1. The $R_4$ substituent may be located on any of the available carbon atoms of the pyridino portion of the compound, i.e., at the 4', 5', 6', or 7' positions. When "c" is 0, there are no non-hydrogen substituents and all of the ring carbon atoms have their full complement of hydrogen atoms.

$R_5$ in graphic formula I is selected from the group consisting of halogen, e.g., chloro, fluoro, or bromo, $C_1-C_5$ alkyl, $C_1-C_5$ alkoxy, nitro, cyano, thiocyano, $C_1-C_4$ monohaloalkyl, e.g., chloromethyl and chloroethyl, $C_1-C_2$ polyhaloalkyl, e.g., trihaloalkyl, such as trifluoromethyl and 2,2,2-trifluoroethyl, and monoalkylamino or dialkylamino wherein the alkyl moiety of the alkylamino group contains from 1 to 4 carbon atoms, e.g., methylamino, dimethylamino and diethylamino. The letter "e" is a integer of from 0 to 3, preferably 1-2. In particular, $R_5$ is $C_1-C_2$ alkyl, $C_1-C_2$ alkoxy, chloro, fluoro, bromo, nitro, or trifluoromethyl.

The $R_5$ substituent(s), i.e., when "e" is 1, may be located on any of the available carbon atoms of the benzo portion of the benzoxazine moiety of the compound, i.e., at the number 5, 6, 7 or 8 carbon atom positions. Preferably, the $R_5$ substituent is present on the number 5, 6, or 7 carbon atoms of the benzoxazine moiety. When "e" is 2 or more, the $R_5$ substituents may be the same or different and in either case are selected from the above-described group. When "e" is 2, the $R_5$ substituents may be located at the number 5 and 6, 5 and 7, 5 and 8, 6 and 7, 7 and 8, or 6 and 8 carbon atom positions, preferably at the number 5 and 7 positions. When "e" is 3, the $R_5$ substituents may be located at the number 5, 6, and 7; 5, 7, and 8; 6, 7, and 8; or 5, 6, and 8 carbon atom positions. When "e" is 0 (zero) there are no non-hydrogen substituents and all of the ring carbon atoms have their full complement of hydrogen atoms.

Of particular interest, are photochromic materials represented by graphic formula I wherein $R_1$ is a $C_1-C_4$ alkyl, such as methyl, ethyl, n-propyl, isopropyl, n-butyl, secondary butyl, isobutyl and tertiary butyl; $R_2$ and $R_3$ are each methyl, ethyl or phenyl; $R_4$ is selected from chloro, fluoro, methyl or methoxy; $R_5$ is selected from methoxy, methyl, nitro, fluoro, bromo or chloro, "c" is 1 or 2, "e" is 1 or 2, and the nitrogen hetero atom of the pyridine ring is located at the 4' or 5' positions. Examples of contemplated compounds represented by formulae II-IV are tabulated in Table I. The prime(') designations for the $R_1$, $R_2$ and $R_3$ substituents have been omitted. Compound 1 in Table I may be named: 1', 3'-Dihydro-1',3',3'-trimethyl-5,7-dimethoxyspiro[2H-1,4-benzoxazine-2,2'[2H]pyrrolo[2,3-b]pyridine]

TABLE I

| Compound/ | $R_1$ | $R_2$ | $R_3$ | $R_4$ | $R_4$ | $R_5$ | $R_5$ | N(Locus) |
|---|---|---|---|---|---|---|---|---|
| 1 | Me | Me | Me | H | H | 5-MeO | 7-MeO | 7' |
| 2 | Me | Me | Et | H | H | 5-MeO | 7-MeO | 7' |
| 3 | Me | Me | Me | 6'-Me | H | 5-MeO | 7-MeO | 7' |
| 4 | Me | Me | Me | 6'-MeO | H | 5-MeO | 7-MeO | 7' |
| 5 | n-Pr | Me | Me | H | H | 5-MeO | 7-MeO | 7' |
| 6 | n-Pr | Me | Et | H | H | 5-MeO | 7-MeO | 7' |
| 7 | n-Pr | Me | Et | 5'-Me | H | 5-MeO | 7-MeO | 7' |
| 8 | n-Pr | Me | Et | 6'-Me | H | 5-MeO | 7-MeO | 7' |
| 9 | Me | Me | Me | H | H | 5-MeO | 7-MeO | 5' |
| 10 | Me | Me | Et | H | H | 5-MeO | 7-MeO | 5' |
| 11 | n-Pr | Me | Me | H | H | 5-MeO | 7-MeO | 5' |
| 12 | n-Pr | Me | Me | 4'-Me | H | 5-MeO | 7-MeO | 5' |
| 13 | n-Pr | Me | Me | 6'-Me | H | 5-MeO | 7-MeO | 5' |
| 14 | Me | Me | Me | H | H | 5-MeO | 7-MeO | 4' |
| 15 | Me | Me | Et | H | H | 5-MeO | 7-MeO | 4' |
| 16 | Me | Me | Me | 5'-Me | H | 5-MeO | 7-MeO | 4' |
| 17 | Me | Me | Me | 6'-Me | H | 5-MeO | 7-MeO | 4' |

Key for Table
Me = Methyl
Et = Ethyl
n-Pr = n-Propyl
MeO = Methoxy

In naming the compounds represented by formulae II-IV, the IUPAC rules of organic nomenclature have been used. The positions on the pyrrolo pyridine portion of the molecule have been numbered clockwise starting with the nitrogen atom as number one (1), and are identified by a prime number, e.g., 3'. The positions on the benzoxazine portion of the molecule have been numbered clockwise starting with the oxygen atom as number one (1). For example, when $R_1$, $R_2$ and $R_3$ are each methyl substituents and "c" and "e" are 0, the compounds thereby represented by graphic formulae II-IV may be named respectively:

(1) 1',3'-Dihydro-1',3',3'-trimethylspiro[2H-1,4-benzoxazine-2,2'-[2H]pyrrolo[2,3-b]pyridine];
(2) 1',3'-Dihydro-1',3',3'-trimethylspiro[2H-1,4-benzoxazine-2,2'-[2H]pyrrolo[3,2-c]pyridine]; and
(3) 1',3'-Dihydro-1',3',3'-trimethylspiro[2H-1,4-benzoxazine-2,2'-[2H]pyrrolo[3,2-b]pyridine].

Other compounds in Table I may be named in the same manner using the aforesaid example and the IUPAC rules by using the indicated substituents.

The photochromic materials of the present invention may be synthesized by condensing an appropriately substituted 2-methylene-1 and 4,5 or 7 diazaindane with an appropriately substituted ortho-nitrosophenol in a hydrocarbon solvent at reflux conditions followed by isolation and purification by chromatography, crystallization, distillation, or trituration. The required reactants, i.e., 2-methylene azaindolenes and ortho-nitrosophenol compounds, may be synthesized using procedures available in the literature. Briefly, the 2-methyleneazaindolenes are prepared by reacting an Nα-methyl-pyridylhydrazine with an appropriate ketone followed by cyclization of the resulting hydrazone under thermal or zinc halide catalyzed conditions. See, for example, "Diazaindenes and Their Quaternary Salts, Part II, The Cyclization of Isopropyl Methyl Ketone 3-Pyridyl Hydrazone," by G. E. Ficken and J. D. Kendell, *Journal of the Chemical Society*, pp 584–588, 1961. The ortho-nitrosophenol compounds are made by reaction of phenol with sodium nitrite in an acidic medium. See, for example, *Organic Synthesis*, Volume 1, 2nd Edition, H. Gilman et al., Ed., John Wiley and Sons, pp 411-412 (1941).

The compounds of the present invention may be dissolved in common organic solvents such as benzene, toluene, chloroform, ethylacetate, methylethylketone, acetone, ethyl alcohol, methyl alcohol, acetonitrile, tetrahydrofuran, dioxane, methyl ether of ethylene glycol, dimethylformamide, dimethylsulfoxide, methyl cellosolve, morpholine, and ethylene glycol. The compounds may also be dispersed in liquids containing water, alcohols and other solvents.

The compounds of the present invention may also be dissolved in colorless or transparent solutions prepared from transparent polymers (or copolymers) or blends of such transparent polymers and a suitable organic solvent, e.g., polymers of transparent host materials described hereinafter dissolved in one or more of the aforesaid described organic solvents. Examples of such solutions include a poly(vinylacetate)-acetone solution, a nitrocellulose-acetonitrile solution, a poly(vinylchloride)-methylethylketone solution, a poly(methyl methacrylate)-acetone solution, a cellulose acetate-dimethylformamide solution, a poly(vinyl pyrrolidone)-acetonitrile solution, a polystyrene-benzene solution, and an ethyl cellulose-methylene chloride solution.

The aforesaid solutions or compositions may be applied to a compatible host material, e.g., a transparent support, such as cellulose triacetate, polyethylene terephthalate or baryta paper and dried to obtain an article that may be color formed by ultraviolet radiation and returned to colorless by removing the source of ultraviolet radiation.

The photochromic compounds described herein (or compositions containing them) may be applied to or incorporated within a coating composition applied to a compatible support; or applied to or incorporated within the article comprising a compatible host, e.g., a polymerized organic material such as a synthetic polymeric plastic host material.

The polymeric host material will usually be transparent, but may be translucent or even opaque. The polymer product need only be transparent to that portion of the electromagnetic spectrum, which activates the photochromic substance, i.e., that wavelength of ultraviolet (UV) light that produces the open form of the substance and that portion of the visible spectrum that includes the absorption maximum wavelength of the substance in its UV activated form, i.e., the open form. Further, the color of the host material should not be such that it masks the color of the activated form of the photochromic compound i.e., so the change in color is readily apparent to the observer.

Preferably, the host material article is a solid transparent material or an optically clear material, e.g., materials suitable for ophthalmic elements, such as plano or ophthalmic lenses, or materials useful for applications such as windows, windshields, aircraft transparencies, etc. A host material containing the photochromic compounds described in connection with the present invention can be used in the preparation of photochromic plastic films, sheets and lenses, such as lenses for sunglasses, ski goggles, visors, camera lenses and variable density filters. As used herein, the term "optical element" is meant to include lenses and transparencies. The photochromic compounds or compositions described herein also may be incorporated into coatings such as paints, inks, etc. by admixing the material with the fluid coating composition before it is applied to the host surface and dried.

Examples of host materials which may be used with the photochromic substances or compositions described herein include polymers of polyol(allyl carbonate), i.e.,: homopolymers and copolymers of polyol(allyl carbonate) monomers, homopolymers and copolymers of polyfunctional acrylate monomers, polyacrylates, poly(alkylacrylates) such as poly(methyl methacrylate), cellulose acetate, cellulose triacetate, cellulose acetate propionate, cellulose acetate butyrate, poly(vinyl acetate), poly(vinyl alcohol), poly(vinyl chloride), poly(vinylidene chloride), polyurethanes, polycarbonates, poly(ethylene terephthalate), polystyrene, copoly(styrene-methyl methacrylate) copoly(styrene-acrylonitrile), polyvinylbutyral and homopolymers and copolymers of diallylidene pentaerythritol, particularly copolymers with polyol (allyl carbonate) monomers, e.g., diethylene glycol bis(allyl carbonate), and acrylate monomers. Transparent copolymers and blends of transparent polymers are also suitable as host materials.

Preferably, the host material is an optically clear polymerized organic material prepared from a polycarbonate resin, such as the carbonate-linked resin derived from bisphenol A and phosgene, which is sold under the trademark, LEXAN; a poly(methyl methacrylate), such as the material sold under the trademark, PLEXIGLAS: polymerizates of a polyol(allyl carbonate), especially diethylene glycol bis(allyl carbonate), which monomer is sold under the trademark CR-39, and its copolymers with for example vinyl acetate, e.g., copolymers of from 80-90 percent diethylene glycol bis(allyl carbonate) and 10-20 percent vinyl acetate; particularly 80-85 percent of the bis(allyl carbonate) and 15-20 percent vinyl acetate, cellulose acetate, cellulose propionate, cellulose butyrate, polystyrene and its copolymers with methyl methacrylate, vinyl acetate and acrylonitrile, and cellulose acetate butyrate.

Polyol (allyl carbonate) monomers which can be polymerized to form a transparent host material are the allyl carbonates of linear or branched aliphatic or aromatic liquid polyols, e.g., aliphatic glycol bis(allyl carbonate) compounds, or alkylidene bisphenol bis(allyl carbonate) compounds. These monomers can be described as unsaturated polycarbonates of polyols, e.g, glycols. The monomers can be prepared by procedures well known in the art, e.g., U.S. Pat. Nos. 2,370,567 and 2,403,113.

The polyol (allyl carbonate) monomers can be represented by the graphic formula:

(V)

wherein R is the radical derived from an unsaturated alcohol and is commonly an allyl or substituted allyl group, R' is the radical derived from the polyol, and n is a whole number from 2-5, preferably 2. The allyl group (R) can be substituted at the 2 position with a halogen, most notably chlorine or bromine, or an alkyl group containing from 1 to 4 carbon atoms, generally a methyl or ethyl group. The R group can be represented by the graphic formula:

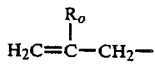 (VI)

wherein $R_o$ is hydrogen, halogen, or a $C_1$-$C_4$ alkyl group. Specific examples of R include the groups: allyl, 2-chloroallyl, 2-bromoallyl, 2-fluoroallyl, 2-methallyl, 2-ethylallyl, 2-isopropylallyl, 2-n-propylallyl, and 2-n-butylallyl. Most commonly R is the allyl group, $CH_2=CH-CH_2-$.

R' is a polyvalent radical derived from the polyol, which can be an aliphatic or aromatic polyol that contains 2, 3, 4 or 5 hydroxy groups. Typically, the polyol contains 2 hydroxy groups, i.e., a glycol or bisphenol. The aliphatic polyol can be linear or branched and contain from 2 to 10 carbon atoms. Commonly, the aliphatic polyol is an alkylene glycol having from 2 to 4 carbon atoms or a poly($C_2$-$C_4$) alkylene glycol, i.e., ethylene glycol, propylene glycol, trimethylene glycol, tetramethylene glycol, or diethylene glycol, triethylene glycol, etc.

The aromatic polyol can be represented by the graphic formula:

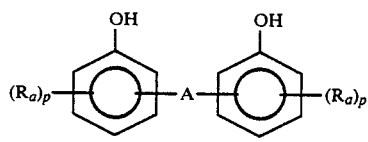 (VII)

wherein A is a bivalent radical derived from an acyclic aliphatic hydrocarbon, e.g., an alkylene or alkylidene radical, having from 1 to 4 carbon atoms, e.g., methylene, ethylene, and dimethylmethylene (isopropylidene). Ra represents a lower alkyl substituent of from 1 to 3 carbon atoms and halogen, e.g., chlorine and bromine, and p is 0, 1, 2, or 3. Preferably, the hydroxyl group is in the ortho or para position.

Specific examples of the radical R' include: alkylene groups containing from 2 to 10 carbon atoms such as ethylene, ($-CH_2-CH_2-$), trimethylene, methylethylene, tetramethylene, ethylethylene, pentamethylene, hexamethylene, 2-methylhexamethylene, octamethylene, and decamethylene; alkylene ether groups such as $-CH_2-O-CH_2-$, $-CH_2CH_2-O-CH_2CH_2-$, $-CH_2-O-CH_2-CH_2-$, and $-CH_2CH_2C-H_2-O-CH_2CH_2CH_2-$; alkylene polyether groups such as $-CH_2CH_2-O-CH_2CH_2-O-CH_2CH_2-$, and $-CH_2CH_2CH_2-O-CH_2CH_2C-$ $H_2-O-CH_2CH_2CH_2-$; alkylene carbonate and alkylene ether carbonate groups such as $-CH_2C-H_2-O-CO-O-CH_2CH_2-$ and $-CH_2C-H_2O-O-CH_2CH_2-O-CH_2CH_2-O-$ $-CH_2C-H_2-$; and isopropylidene bis(para-phenyl), i.e., 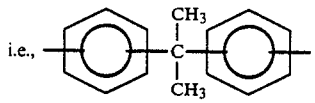

Most commonly, R' is $-CH_2CH_2-$, $-CH_2C-H_2-O-CH_2CH_2-$; or $-CH_2CH_2-O-CH_2C-H_2-O-CH_2CH_2-$.

Specific examples of polyol (allyl carbonate) monomers include ethylene glycol bis(2-chloroallyl carbonate), ethylene glycol bis(allyl carbonate), diethylene glycol bis(2-methallyl carbonate), diethylene glycol bis(allyl carbonate), triethylene glycol bis(allyl carbonate), propylene glycol bis(2-ethylallyl carbonate), 1,3-propanediol bis(allyl carbonate), 1,3-butanediol bis(allyl carbonate), 1,4-butanediol bis(2-bromoallyl carbonate), dipropylene glycol bis(allyl carbonate), trimethylene glycol bis(2-ethylallyl carbonate), pentamethylene glycol bis(allyl carbonate), and isopropylidene bisphenol bis(allyl carbonate).

Industrially important polyol bis(allyl carbonate) monomers which can be utilized in the invention herein contemplated are:

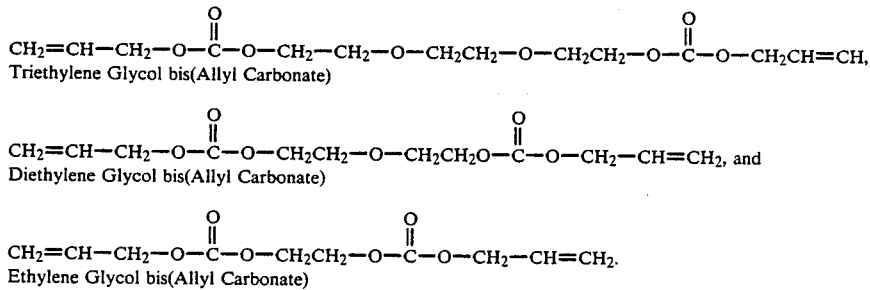

Diethylene glycol bis(allyl carbonate) is preferred.

Because of the process by which the polyol(allyl carbonate) monomer is prepared, i.e., by phosgenation of the polyol (or allyl alcohol) and subsequent esterification by the allyl alcohol (or polyol), the monomer product can contain related monomer species in which the moiety connecting the allyl carbonate groups contains one or more carbonate groups. These related monomer species can be represented by the graphic formula:

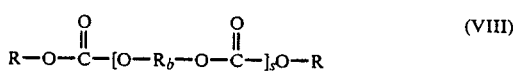 (VIII)

wherein defined above, $R_b$ is a bivalent radical, e.g., alkylene or phenylene, derived from a diol, and s is a whole number from 2 to 5. The related monomer species of diethylene glycol bis(allyl carbonate) can be represented by the graphic formula,

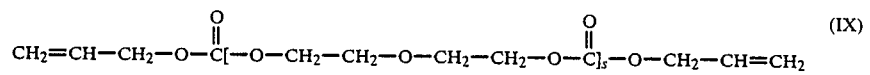 (IX)

wherein s is a whole number from 2 to 5. The polyol (allyl carbonate) monomer can typically contain from 2 to 20 weight percent of the related monomer species and such related monomer species can be present as mixtures, i.e., mixtures of the species represented by s being equal to 2, 3, 4 etc.

In addition, a partially polymerized form of the polyol (allyl carbonate) monomer, i.e., prepolymer, can be used. In that embodiment, the monomer is thickened by heating or partially polymerized by using small, e.g., 0.5–1.5 parts of initiator per hundred parts of monomer (phm), to provide a non-gel containing, more viscous monomeric material.

As used in the present description and claims, the term polyol(allyl carbonate) monomer or like names, e.g., diethylene glycol bis(allyl carbonate), are intended to mean and include the named monomer or prepolymer and any related monomer species contained therein.

Polyfunctional acrylate monomers that may be used to prepare synthetic polymeric host materials are esterification products of an acrylic acid moiety selected from the group consisting of acrylic acid and methacrylic acid, and a polyol, e.g., a diol, a triol or tetracarbinol. More particularly, the polyfunctional acrylate monomer may be represented by the following graphic formula:

$$(CH_2=C(R_t)-C(O))_{\overline{n}}R'' \qquad (X)$$

wherein $R_t$ is hydrogen or methyl, n is the number 2, 3, or 4, and $R''$ is the multivalent radical, i.e., a bivalent, trivalent or quadravalent radical, remaining after removal of the hydroxy groups from a polyol having from 2 to 4 hydroxy groups, e.g., a diol, a triol or tetracarbinol respectively. More particularly, $R_t$ is hydrogen or methyl, and n is 2 or 3, more usually 2.

$R''$ may be selected from the group consisting of alpha, omega $C_2$–$C_8$ glycols, cyclohexane diol, diethylene glycol, triethylene glycol, tetraethylene glycol, dipropylene glycol, $C_2$–$C_5$ triols and pentaerythritol. Examples of such polyols include ethylene glycol, trimethylene glycol, 1,4-butane diol, 1,5-pentane diol, 1,6-hexane diol, propylene glycol, trimethylol propane, glycerol and the like.

Examples of polyfunctional acrylate monomers, such as diacrylates and triacrylates, include: ethylene glycol diacrylate, ethylene glycol dimethyacrylate, 1,2-propane diol diacrylate, 1,3-propane diol diacrylate, 1,2-propane diol dimethacrylate, 1,3-propane diol dimethacrylate, 1,4-butane diol diacrylate, 1,3-butane diol dimethacrylate, 1,4-butane diol dimethacrylate, 1,5-pentane diol diacrylate, 2,5-dimethyl-1,6-hexane diol dimethacrylate, diethylene glycol diacrylate, diethylene glycol dimethacrylate, triethylene glycol dimethacrylate, trimethylol propane trimethacrylate, tetraethylene glycol diacrylate, tetraethylene glycol dimethacrylate, dipropylene glycol diacrylate, dipropylene glycol dimethacrylate, trimethylol propane triacrylate, glycerol triacrylate, glycerol trimethacrylate, pentaerythritol triacrylate, pentaerythritol dimethacrylate, pentaerythritol tetraacrylate, pentaerythritol tetramethacrylate and mixtures of such acrylate monomers.

A portion of the polyfunctional acrylate monomer may be replaced with a monofunctional copolymerizable monomer containing the vinyl ($CH_2=CH-$) grouping. Such compatible monomers include monofunctional acrylic and methacrylic acid esters, and vinyl esters of $C_2$–$C_6$ carboxylic acids, i.e., vinyl carboxylates.

Preferably, the copolymerizable monomer is a non-aromatic, e.g., non-benzenoid, containing monomer. Monofunctional acrylic or methacrylic ester monomers may be graphically illustrated by the following formula,

$$CH_2=C(R_t)-C(O)-O-R''' \qquad (XI)$$

wherein $R_t$ is hydrogen or methyl, and $R'''$ is selected from the group consisting of $C_1$–$C_{12}$, e.g., $C_1$–$C_8$, alkyl, $C_5$–$C_6$ cycloalkyl, glycidyl and hydroxyethyl. Preferably, $R'''$, is a $C_1$–$C_4$ alkyl, e.g., methyl or cyclohexyl.

Examples of monofunctional acrylic acid type monomers include, for example, the acrylic and methacrylic acid esters of alkanols such as methanol, ethanol, propanol, butanol, pentanol, hexanol, heptanol and octanol, e.g., methyl acrylate, methyl methacrylate, ethyl acrylate and ethyl methacrylate, cycloalkanols such as cyclopentanol and cyclohexanol, glycidol (3-hydroxy propylene oxide, (d, l, dl)) and ethylene glycol. Examples of vinyl carboxylates include vinyl acetate, vinyl propionate, vinyl butyrate and vinyl valerate. In addition to and/or in place of the aforedescribed monofunctional copolymerizable monomer, monofunctional allylic and difunctional allylic copolymerizable compatible monomers may also replace a portion of the polyfunctional acrylate monomer. Monofunctional allylic monomers contemplated include allyl esters of $C_2$–$C_6$ carboxylic acids, $C_1$–$C_6$ allyl ethers and other copolymerizable allyl compounds. Preferably the monofunctional allylic monomer is a non-aromatic compound. Difunctional allylic copolymerizable monomers contemplated herein are the polyol (allyl carbonates) monomers of graphic formula V.

The amount of photochromic compound or composition-containing same applied to or incorporated into a host material is not critical provided that a sufficient amount is used to produce a photochromic effect discernible to the naked eye. Generally such amount can be described as a photochromic amount. The amount used depends often upon the intensity of color desired upon irradiation thereof and upon the method used to incorporate or apply the photochromic substances. Typically, the more compound applied or incorporated, the greater is the color intensity. Usually, the amount of each photochromic substance incorporated into or applied to the host material ranges from about 0.01 to about 20 percent by weight, more usually from about 0.05 to about 10 percent by weight, based on the weight of the host material. Stated another way, the amount of each photochromic substance used to impart a photochromic effect will typically vary from about 0.1 to about 10, e.g., 0.5 to 2 milligrams of the photochromic substance per square inch of the surface of the host material independent of the thickness of the host material article. Hence, the photochromic substance is present in higher concentrations in thin samples, films, or coatings, and in lower concentrations in thick samples.

The photochromic compounds or compositions containing same may be applied to or incorporated into a host material by methods known in the art. Such methods include dissolving or dispersing the compound within the host material, e.g., imbibition of the photochromic compound into the host material, by immersion or thermal transfer; incorporation of the photochromic compound as a separate layer between adjacent layers of the host material; and applying the photochromic substance as a coating to the host material. The term "imbibition" or "imbibe" is intended to mean and include permeation of the photochromic substance alone into the host material, solvent assisted transfer, absorption of the photochromic substance into a porous polymer, vapor phase transfer, and other such transfer mechanisms. For example:

(a) The photochromic compounds or compositions containing same may be mixed with a polymerizable composition that, upon curing, produces a polymeric host material and the polymerizable composition cast as a film, sheet or lens, injection molded or otherwise formed into a sheet or lens, or polymerized by emulsion or suspension polymerization to form a photochromic particulate material that may be used as a pigment;

(b) The photochromic compounds may be dissolved or dispersed in water, alcohol or other solvents or solvent mixtures and then imbibed into the solid host material by immersion of the solid host material for from several minutes to several hours, e.g., 2-3 minutes to 2-4 hours, in a bath of such solution or dispersion. The bath is conventionally at an elevated temperature, usually in the range of 50°-120° C.; however, higher temperatures may be used. Thereafter, the host material is removed from the bath and dried;

(c) The photochromic compounds and compositions containing same may also be applied to the surface of the host material by any convenient manner, such as spraying, brushing, spin-coating or dip-coating from a solution or dispersion of the photochromic compound in the presence of a polymeric binder. Thereafter, the photochromic compound is imbibed into the host material by heating it, e.g, in an oven, for from a minute to several hours at temperatures in the range of from 80°-180° C.;

(d) In a variation of the preceding imbibition procedure, the photochromic compound or composition containing same may be deposited onto or absorbed by a temporary support, e.g., a sheet of kraft paper, aluminum foil, polymer film or fabric, which is then placed in near proximity or in contact with the host material and heated, e.g., in an oven. This and the preceding procedure may be repeated one or more times to imbibe the desired amount of photochromic compound into the host material;

(e) The photochromic compound may be dissolved or dispersed in a transparent polymeric material which may be applied to the surface of the host in the form of an adherent film by any suitable technique such as spraying, brushing, spin-coating or dip-coating; and finally (f) The photochromic compound may be incorporated in or applied to a transparent polymeric material by any of the above-mentioned methods, which can then be placed within the host material as a discrete layer intermediate to adjacent layers of the host material(s).

In addition, imbibition of photochromic compounds into a host material may be accomplished by the method described in U.K. Patent Application No. 2,174,711, which is hereby incorporated in toto by reference. In that method a substantially mottle-free, substantially homogeneous film of polymeric resin having the photochromic compound dissolved therein is applied to the surface of the host material. The film-bearing host material is heated to temperatures near to but below the melting temperature of the photochromic compound for a time sufficient to incorporate a photochromic amount of the photochromic compound into the surface of the host. The photochromic-lean film is then removed from the host surface with a suitable solvent.

Adjuvant materials may also be incorporated into the host with the photochromic compounds prior to or subsequent to their application or incorporation into the host material. For example, ultraviolet light absorbers may be admixed with the photochromic compounds before their application to the host material or such absorbers may be superposed, e.g., superimposed, as a layer between the photochromic compound and the incident light. Further, stabilizers may be admixed with the photochromic compound prior to their application to the host material to improve the light fatigue resistance of the photochromic compound Stabilizers such as hindered amine light stabilizers and singlet oxygen quenchers, such as a nickel ion complex with an organic ligand, are contemplated. They may be used alone or in combination. Such stabilizers are described in European patent application No. 195,898.

Compatible (chemically and color-wise) tints, i.e., dyes, may be applied to the host material to achieve a more aesthetic result, for medical reasons, or for reasons of fashion. The particular dye selected will vary and depend on the aforesaid need and result to be achieved. In one embodiment, the dye may be selected to complement the color resulting from the activated photochromic substances, e.g., to achieve a more neutral color or absorb a particular wavelength of incident light. In another embodiment, the dye may be selected to provide a desired hue to the host matrix when the photochromic compounds are unactivated. Finally, appropriate protective coating(s) may be applied to the surface of the host material. These may be abrasion resistant coatings or coatings that serve as oxygen barriers, e.g., a polyvinyl alcohol coating. Such coatings are known in the art.

The present invention is more particularly described in the following examples which are intended as illustrative only since numerous modifications and variations therein will be apparent to those skilled in the art.

EXAMPLE 1

A reaction vessel wrapped with a heating mantle was charged with 500 milliliters of methoxyethanol and 56.8 grams (47.3 milliliters) of 2-chloropyridine. 46.0 grams (53.2 milliliters) of methylhydrazine were then added dropwise to that solution through an addition funnel. The resulting mixture was heated under a nitrogen blanket to about 110° C. and allowed to reflux for 48 hours. Power to the heating mantle was then turned off and the reaction mixture allowed to cool with stirring to room temperature. The cooled reaction mixture was held over a weekend (about 72 hours). During this period the reaction mixture was stirred continuously. The reaction mixture was then heated under vacuum to remove most of the methoxyethanol solvent and then permitted to cool down overnight.

200 milliliters of a 10 weight percent sodium hydroxide solution were added to the resulting cooled reaction mixture. The reaction product was extracted with three-100 milliliter portions of ether and placed over potassium carbonate to dry. The ether was then removed from the reaction product under vacuum and the product held overnight under a nitrogen pad. In the morning, a precipitate in the product was observed. The product was distilled to recover Nα-methyl-2-pyridylhydrazine. Distillation was conducted under a vacuum of 25 millimeters of mercury and the fraction between 142° C. and 154° C. collected. Distillation produced a clear, slightly yellowish liquid. Confirmation of the product as Nα-methyl-2-pyridylhydrazine was by appropriate spectral analysis.

A 100 milliliter round bottom three-necked flask was charged with 40 milliliters of benzene and 10.91 gram of the N α-methyl-2-pyridylhydrazine product produced as previously described. The flask was then charged with 12.9 grams (16.0 milliliters) of 3-methyl-2-butanone. A Dean-Stark trap was put on the middle neck with a condenser and nitrogen purge. The mixture in the flask was heated to reflux and water was removed as an azeotrope. Refluxing continued for 23 hours after which the remaining solvent was removed by distillation. The resulting product, which contained a small amount of benzene, was transferred to a three-necked 100 milliliter round bottom flask. 0.3 grams of anhydrous zinc chloride was added to the flask and the contents heated to 150° C. After 1½ hours at temperature, the reaction mixture was permitted to cool overnight and then vacuum distilled with a Vigreaux column. A yellowish mixture distilled over at 100° C. at 12 millimeters of mercury. Further purification of the distillate was performed by a second distillation at a pressure of 11 millimeters of mercury. The fraction at 70°-80° C. was collected. The product, i.e., 1,3,3-trimethyl-2-methylene-1,7-diazaindane, was confirmed by appropriate spectral analysis.

Into a three-necked 100 milliliter round bottom flask was charged a solution of 0.8 grams of the thus prepared 1,3,3-trimethyl-2-methylene-1,7-diazaindane in 20 milliliters of absolute ethanol. The solution was heated under a nitrogen pad to 60°-65° C. and 0.84 grams of 2-nitroso-3,5-dimethoxyphenol added to the flask. The reaction mixture was maintained at temperature and refluxing for a total reaction time of about 26 hours. The ethanol was removed on a rotary evaporator and the resulting reaction mixture taken up in ether and filtered. The ether solution sequentially was washed with 100 milliliters of a 10 percent sodium hydroxide solution, and 100 milliliters of a saturated sodium chloride solution and then dried over potassium carbonate. The ether was removed under vacuum. A silica gel column was used to isolate the final product, i.e., 1',3'-Dihydro-1',3',3'-trimethyl-5,7-dimethoxyspiro-[2H-1,4-benzoxazine-2,2'-[2H] pyrrolo[2,3-b]pyridine]. Identification of the product was confirmed by appropriate spectral analysis.

EXAMPLE 2

Into a three-necked 100 milliliter round bottom flask equipped with a Dean-Stark trap was charged 10.91 grams of Nα-methyl-2-pyridylhydrazine, 40 milliliters of benzene and 15.0 grams of 3-methyl-2-pentanone. The mixture was heated to reflux temperatures allowing water to be removed as an azeotrope. The reaction was conducted for about 72 hours. After removal of benzene from the reaction mixture by vacuum distillation, 0.3 grams of zinc chloride was added to the reaction mixture. The internal temperature of the mixture reached 220° C. and was maintained at that temperature for about 5 hours. The resulting product found was identified as 1,3-dimethyl-3-ethyl-2-methylene-1,7-diazaindane by appropriate spectral analysis.

5.0 grams of the thus prepared 1,3-dimethyl-3-ethyl-2-methylene-1,7-diazaindane product were added to about 80 milliliters of ethanol and warmed in a 100 milliliter round bottom flask. When the internal temperature of the flask contents reached 60° C., 3.3 grams of 2-nitroso-3,5-dimethoxyphenol were added to the flask. The mixture was allowed to reflux overnight. The reaction mixture was allowed to cool down and a silica gel column was used to isolate the desired product, i.e., 1',3'-Dihydro-1',3'-dimethyl-3'-ethyl- 5,7-dimethoxyspiro-[2H-1,4-benzoxazine-2,2'-[2H]pyrrolo[2,3-b]pyridine]. Identification was confirmed by appropriate spectral analysis.

EXAMPLE 3

A three-necked 100 milliliter round bottom flask was charged with 25.0 grams of 2-chloro-6-methylpyridine, 20.65 grams of methylhydrazine and 200 milliliters of methoxyethanol. The resulting mixture was refluxed for about 48 hours at which time an additional 20 grams of methylhydrazine was added to the flask to drive the reaction to completion. Refluxing was continued for another 48 hours.

The methoxy ethanol was removed and the product, N α-methyl-6-methyl-2-pyridylhydrazine, washed with 100 milliliters of a 5 percent sodium hydroxide solution and extracted three times with methylene chloride. The methylene chloride was removed using a rotary evaporator. A yellowish-white solid was isolated and identified as the aforesaid pyridylhydrazine product by appropriate spectral analysis.

A 100 milliliter three-necked round bottom flask equipped with a Dean-Stark trap was charged with 40 milliliters of benzene and 15.0 grams of the thus prepared N α-methyl-6-methyl-2-pyridylhydrazine. Subsequently, 16.0 milliliters of 3-methyl-2-butanone were added to the flask and the mixture stirred for ½ hour at room temperature. The contents of the reaction flask were heated slowly to reflux temperatures allowing water to be removed as an azeotrope. The reaction mixture was maintained at the refluxing temperature for 2 hours. Benzene was removed form the reaction mixture under reduced pressure. The resulting product needed no further purification. 0.6 grams of zinc chloride were added to the flask and the mixture heated under a nitrogen pad to 220° C. The reaction mixture was cooled and distillation apparatus attached to the flask A clear, colorless liquid distilled over at 71°-72° C. at 7 millimeters of mercury. The liquid product was identified as 1,3,3,6-tetramethyl-2-methylene-1,7-diazaindane by appropriate spectral analysis.

About 5 grams of the 1,3,3,6-tetramethyl-2-methylene-1,7-diazaindane was added to 60 milliliters of ethanol and heated to 60° C. Thereafter, 3.0 grams of 2-nitroso-3,5-dimethoxyphenol were added to the reaction mixture and the temperature brought to 78° C. The reaction mixture was refluxed overnight and then transferred into a 250 milliliter round bottom flask and put on a rotary evaporator to remove the ethanol. The crude product was isolated using a silica gel column and crystallized from an ether-hexane mixture. The crystallized product was identified as 1',3'-Dihydro-1',3',3'6'-tetramethyl-5,7-dimethoxyspiro-[2H-1,4-benzoxazine-2,2'-[2H]pyrrolo[2,3-b]pyridine] by appropriate spectral analysis.

EXAMPLE 4

25 grams of 4-chloropyridine hydrochloride were added to 100 milliliters of a 25 percent aqueous sodium hydroxide solution and 200 milliliters of methylene chloride. The mixture was stirred for about one hour under a nitrogen atmosphere. The methylene chloride fraction was separated from the aqueous fraction and dried over potassium carbonate. The dried methylene chloride fraction was evaporated to dryness.

The resulting solid residue (4-chloropyridine) was transferred to a 250 milliliter three-necked round bottom flask containing 100 milliliters of methoxyethanol. 23.4 grams (27 milliliters) of methyl hydrazine were added to the flask and the contents of the flask heated. The reaction was conducted at reflux for two hours after which the reaction mixture was allowed to cool to room temperature and held overnight while being stirred. A distillation head was attached to the flask and the methoxyethanol removed by first atmospheric and then subatmospheric distillation. A solid product formed in the flask, which was dissolved in water, washed with 25 percent aqueous caustic and extracted with methylene chloride. The methylene chloride was removed under vacuum leaving a white solid, which was identified as N α-methyl-4-pyridylhydrazine by appropriate spectral analysis.

21 grams of the thus prepared hydrazine product were charged to a 200 milliliter round bottom flask with about 150 milliliters absolute ethanol and 29 gram (36.2 milliliters) of 3-methyl-2-butanone. The reaction mixture was heated to reflux (about 78° C.) and allowed to reflux for about 24 hours. The reaction mixture was held overnight at room temperature and then heated again to reflux temperature whereupon about 2 milliliters of acetic acid were added to the reaction flask. The reaction was conducted for about 8 hours, then allowed to cool to room temperature and held overnight. The ethanol was removed under reduced pressure and the resulting product, i.e., N α-methyl-4-pyridylhydrazone, was identified by appropriate spectral analysis.

10 grams of the thus prepared hydrazone product and 0.3 grams of zinc iodide were mixed and heated to 170° C. The reaction was conducted for 2 hours and 10 minutes. The reaction mixture was cooled down and a distillation head attached to the flask. The product collected at 100° C. at a vacuum of 0.3 millimeters of mercury was identified as 1,3,3-trimethyl-2-methylene-1,5-diazaindane.

A 50 milliliter three-necked round bottom flask was charged with 4.0 grams of the thus prepared diazaindane and about 25 milliliters of absolute ethanol. The contents of the flask were heated to about 60° C. and 4.2 grams of 3,5-dimethoxy-2-nitrosophenol added to the flask. The contents were held at room temperature overnight. The ethanol was removed under vacuum and the crude product isolated using a silica gel column. The product was purified by crystallization from an ether-hexane mixture and identified as 1',3'-Dihydro-1',3',3'-trimethyl-5,7-dimethyl oxyspiro-[2H-1,4-benzoxazine-2,2'-[2H]pyrrolo[3,2-]pyridine] by appropriate spectral analysis.

EXAMPLE 5

A 250 milliliter round bottom flask was charged with 25.0 grams of 2-chloro-6-methoxy pyridine and 200 milliliters of methoxyethanol. To the resulting solution was added slowly 23.5 grams (27 milliliters) of methyl hydrazine. The reaction mixture was stirred for 30 minutes at room temperature, then slowly heated to 90° C., and maintained at such temperature for about 16 hours. The methoxyethanol solvent was removed from the reaction product under reduced pressure leaving solid precipitate. The precipitate was washed with a 5 percent aqueous sodium hydroxide solution and extracted with three 100 milliliter portions of methylene chloride. The methylene chloride was removed under reduced pressure to produce the product, N α-methyl-6-methoxy-2-pyridylhydrazine.

9.0 grams of the thus prepared product, N α-methyl-6-methoxy-2-pyridylhydrazine, and 60 milliliters of benzene were added to a 100 milliliter round bottom flask equipped with a Dean-Stark trap. 9.1 grams (11.3 milliliters) of 3-methyl-butanone were added to the flask and the reaction mixture heated rapidly to 80° C. Water was removed from the flask as an azeotrope during the reaction which was completed in 6 hours. Benzene was removed form the reaction mixture under vacuum and the resulting product mixed with 0.3 grams of zinc chloride. The reaction mixture was heated to 245° C. The reaction was completed in 2 hours. The contents of the flask were distilled under a vacuum of 7 millimeters of mercury and the fraction between 80° C. and 90° C. collected. The product was confirmed as 1,3,3-trimethyl-6-methoxy-2-methylene-1,7-diazaindane by appropriate spectral analysis.

3.2 grams of the thus prepared 1,3,3-trimethyl-6-methoxy-2-methylene-1,7-diazaindane and 60 milliliters of absolute ethanol were mixed in a 100 milliliter round bottom flask and the mixture heated to 60° C. 3.0 grams of 3,5-dimethoxy-2-nitrososphenol were added to the mixture and the resultant mixture refluxed for 24 hours. Ethanol was removed under vacuum and the product isolated by washing with ether, 10 percent aqueous sodium hydroxide and saturated aqueous sodium chloride solution. The product was dried and purified by silica gel chromatography. The isolated product, i.e., 1',3'-Dihydro-1',3',3'-trimethyl-5,6',7-trimethoxyspiro-[2H-1,4-benzoxazine-2,2'-[2H] pyrrolo[2,3-b]pyridine], was confirmed by appropriate spectral analysis.

EXAMPLE 6

To a 250 milliliter dry round bottom flask equipped with magnetic stirrer, heating mantle, reflux condenser and nitrogen inlet tube was charged 25 milliliters of absolute ethanol and 5.0 grams of a mixture containing about 1.23 grams of 1,3,3-trimethyl-2-methylene-1,4-diazaindane. The contents of the flask were heated and just before the contents started to reflux, 0.4 grams of 3,5-dimethoxy-2-nitrosophenol were added. When the contents began to reflux, 600 milligrams of the nitrosophenol were added to the reaction flask. Further amounts of the nitrosophenol were added to the reaction flask while the contents were refluxing as follows: 200 milligrams after 2 hours and 400 milligrams after 2.5 hours. The reaction mixture was cooled and left stirring under a nitrogen atmosphere for 16 hours. The reaction mixture was heated to reflux temperature and additional amounts of the nitrosophenol added as follows: 200 milligrams after 3 hours, and 300 milligrams after 4 hours. The reaction mixture was cooled to eliminate reflux after a total of 5 hours of refluxing. (Total time in reflux was 7.5 hours). Ethanol was removed with a rotovap and the residue purified using silica gel chromatography and trituration with ether. The resulting product, i.e., 1',3'-Dihydro-1',3',3'-trimethyl-5,7-dimethoxyspiro-[2H-1,4-benzoxazine-2,2'-[2H]pyrrolo[3,2-b]pyridine, was confirmed by appropriate spectral analysis.

Although the present invention has been described with reference to the specific details of certain embodiments thereof, it is not intended that such details should be regarded as limitations upon the scope of the invention except as and to the extent that they are included in the accompanying claims.

We claim:

1. A compound represented by the following graphic formula:

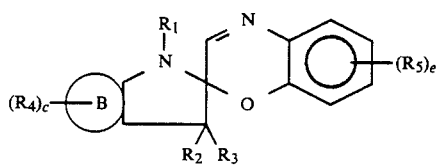

wherein ring B is a pyridine ring fused to the pyrrolo segment of the compound and wherein, (a) $R_1$ is selected from the group consisting of $C_1-C_8$ alkyl, allyl, acrylyl($C_2-C_6$)alkyl, methacrylyl($C_2-C_6$)alkyl, carboxy($C_2-C_6$)alkyl, cyano($C_2-C_6$)alkyl, $C_1-C_4$ acyloxy-($C_2-C_6$)alkyl, hydroxy($C_2-C_6$)alkyl, $(C_2H_4O)_m \cdot CH_3$, and $C_1-C_3$ alkoxy($C_1-C_3$)alkyl, m being a number from 1 to 6;

(b) $R_2$ and $R_3$ are each selected from the group consisting of $C_1-C_5$ alkyl, phenyl, and mono- and di-substituted phenyl, benzyl or combine to form a cyclic ring selected from the group consisting of an alicyclic ring containing from 6 to 8 carbon atoms (including the spiro carbon atom), norbornyl and adamantyl, said phenyl substituents being selected from $C_1-C_4$ alkyl and $C_1-C_5$ alkoxy;

(c) $R_4$ is selected from the group consisting of $C_1-C_5$ alkyl, and $C_1-C_5$ alkoxy;

(d) $R_5$ is selected form the group consisting of $C_1-C_5$ alkyl, and $C_1-C_5$ alkoxy; and (e) the letters "c" and "e" are integers of from 0-1 and 0-3 respectively.

2. A compound of claim 1 wherein:

(a) $R_1$ is selected from the group consisting of $C_1-C_4$ alkyl, carboxy($C_2-C_4$)alkyl, cyano ($C_2-C_4$)alkyl, $C_1-C_4$ acyloxy($C_2-C_4$)alkyl, hydroxy($C_2-C_4$)alkyl, $(C_2H_4O)_m \cdot CH_3$, and $C_1-C_3$alkoxy($C_1-C_3$)alkyl, wherein m is a number of from 1 to 3, (b) $R_2$ and $R_3$ are each selected from $C_1-C_5$ alkyl, and phenyl, (c) $R_4$ is selected from the group consisting of $C_1-C_2$ alkyl, and $C_1-C_2$ alkoxy, (d) $R_5$ is selected from the group consisting of $C_1-C_2$ alkyl, and $C_1-C_2$ alkoxy, and (e) the letter "c" is the integer 0 or 1, and the letter "e" is an integer of from 1 to 2.

3. A compound of claim 2 that is represented by one of the graphic formulae:

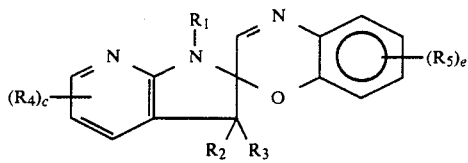

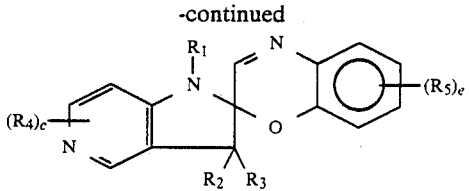

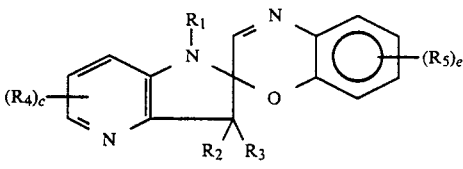

wherein $R_1$, $R_2$, $R_3$, $R_4$, $R_5$, c and e are as defined in claim 2.

4. A compound of claim 3 wherein $R_1$ is $C_1-C_4$ alkyl, $R_2$ and $R_3$ are each methyl or ethyl, $R_4$ is methyl, ethyl or methoxy, $R_5$ is methyl, ethyl, methoxy, or ethoxy, the letter "c" is the integer 0 or 1 and the letter "e" is the integer 1 or 2.

5. A compound of claim 4 wherein when e is 1, the substituent is located at the number 7 carbon atom position, and when is 2, the substituents are located at the numbers 6 and 7 or 5 and 7 carbon atom positions.

6. A compound of claim 3 wherein when e is 1, the substituent is located at the number 7 carbon atom position, and when e is 2, the substituent are located at the numbers 6 and 7 or 5 and 7 carbon atom positions.

7. A compound of claim 1 wherein when e is 1, the substituent is located at the number 7 carbon atom position, and when e is 2, the substituents are located at the numbers 6 and 7 or 5 and 7 carbon atom positions.

8. An article comprising a polymerized organic host material and a photochromic amount of a photochromic compound represented by the graphic formula:

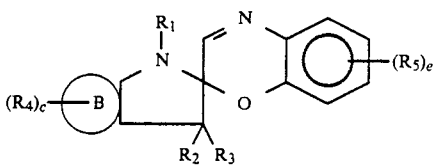

wherein ring B is a pyridine ring fused to the pyrrolo segment of the compound and wherein, (a) $R_1$ is selected from the group consisting of $C_1-C_8$ alkyl, allyl, acrylyl($C_2-C_6$)alkyl, methacrylyl($C_2-C_6$)alkyl, carboxy($C_2-C_6$)alkyl, cyano($C_2-C_6$)alkyl, $C_1-C_4$ acyloxy ($C_2-C_6$)alkyl, hydroxy ($C_2-C_6$)alkyl, $(C_2H_4O)_m \cdot CH_3$, and $C_1-C_3$ alkoxy($C_1-C_3$)alkyl, m being a number from 1 to 6;

(b) $R_2$ and $R_3$ are each selected from the group consisting of $C_1-C_5$ alkyl, phenyl, and mono- and di-substituted phenyl, benzyl or combine to form a cyclic ring selected from the group consisting of an alicyclic ring containing from 6 to 8 carbon atoms (including the spiro carbon atom), norbornyl and adamantyl, said phenyl substituents being selected from $C_1-C_4$ alkyl and $C_1-C_5$ alkoxy;

(c) $R_4$ is selected from the group consisting of $C_1-C_5$ alkyl, and $C_1-C_5$ alkoxy;

(d) $R_5$ is selected form the group consisting of $C_1-C_5$ alkyl, and $C_1-C_5$ alkoxy; and (e) the letters "c" and "e" are integers of from 0-1 and 0-3 respectively.

9. The photochromic article of claim 8 wherein the organic host material is selected from the group consisting essentially of polymers of polyol(allyl carbonate), polyacrylates, poly(alkylacrylates), homopolymers and copolymers of polyfunctional acrylate monomers, cellulose acetate, cellulose triacetate, cellulose acetate propionate, cellulose acetate butyrate, poly(vinyl acetate), poly(vinyl alcohol), poly(vinyl chloride), poly(vinylidene chloride), polycarbonates, polyurethanes, polystyrene, poly(ethylene terephthalate), copoly(styrene-methylmethacrylate), copoly(styrene-acrylonitrile), polyvinylbutyral, and homopolymers of diallylidene pentaerythritol and its copolymers with polyol(allyl carbonate) monomer or acrylate monomer.

10. The photochromic article of claim 9 wherein the organic host material is a transparent polymer of polyol(allyl carbonate) selected from poly and copolymers of polyol(allyl carbonate) and vinyl acetate.

11. The photochromic article of claim 9 wherein the photochromic compound is represented by one of the graphic formulae:

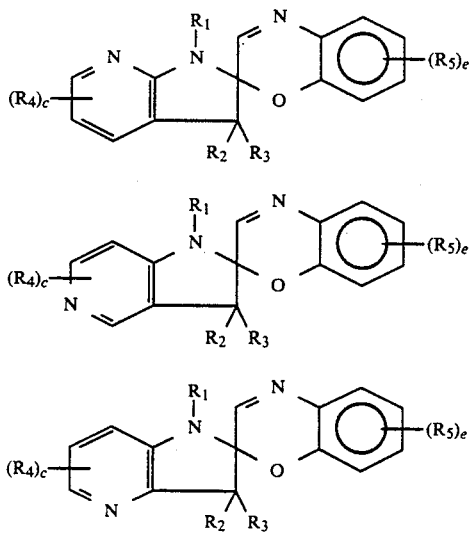

wherein:
(a) $R_1$ is selected from the group consisting of $C_1$-$C_4$ alkyl, carboxy($C_2$-$C_4$)alkyl, cyano ($C_2$-$C_4$)alkyl, $C_1$-$C_4$ acyloxy($C_2$-$C_4$)alkyl, hydroxy($C_2$-$C_4$)alkyl, $(C_2H_4O)_m \cdot CH_3$, wherein m is a number of from 1 to 3, and $C_1$-$C_3$ alkoxy($C_1$-$C_3$)alkyl,
(b) $R_2$ and $R_3$ are each selected from $C_1$-$C_5$ alkyl and phenyl,
(c) $R_4$ is selected from the group consisting of $C_1$-$C_2$ alkyl, and $C_1$-$C_2$ alkoxy,
(d) $R_5$ is selected from the group consisting of $C_1$-$C_2$ alkyl, and $C_1$-$C_2$ alkoxy, and
(e) the letter "c" is an integer of from 0 to 1, and the letter "e" is an integer of from 1 to 2.

12. The article of claim 11 wherein when e is 1, the substituent is located at the number 7 carbon atom position, and when e is 2, the substituents are located at the numbers 6 and 7 or 5 and 7 carbon atom positions.

13. The article of claim 9 wherein when e is 1, the substituent is located at the number 7 carbon atom position, and when e is 2, the substituents are located at the numbers 6 and 7 or 5 and 7 carbon atom positions.

14. A photochromic article comprising a solid transparent polymerized organic host material selected from the group consisting of polycarbonates, polymers of polyol (allyl carbonate), poly(methylmethacrylate), cellulose acetate, cellulose propionate, cellulose butyrate, cellulose acetate butyrate, polystyrene, copoly(styrene-methylmethacrylate) copoly(styrene-acrylonitrile), and homopolymers of diallylidene pentaerythritol and its copolymers with polyol(allyl carbonate) monomer or acrylate monomer, and a photochromic amount of a photochromic compound represented by the graphic formula:

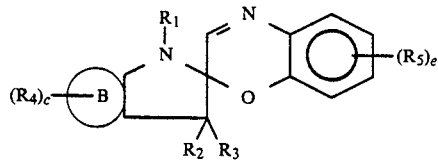

wherein ring B is a pyridine ring fused to the pyrrolo segment of the compound and wherein:
(a) $R_1$ is selected from the group consisting of $C_1$-$C_4$ alkyl, carboxy($C_2$-$C_4$)alkyl, cyano($C_2$-$C_4$)alkyl, $C_1$-$C_4$ acyloxy($C_2$-$C_4$)alkyl, hydroxy($C_2$-$C_4$)alkyl, $(C_2H_4O)_m \cdot CH_3$, and $C_1$-$C_2$ alkoxy($C_1$-$C_2$)alkyl, wherein m is a number of from 1 to 3,
(b) $R_2$ and $R_3$ are each selected from $C_1$-$C_5$ alkyl and phenyl,
(c) $R_4$ is selected from the group consisting of $C_1$-$C_2$ alkyl, and $C_1$-$C_2$ alkoxy,
(d) $R_5$ is selected from the group consisting of $C_1$-$C_2$ alkyl, and $C_1$-$C_2$ alkoxy, and
(e) the letter "c" is an integer of from 0 to 1, and the letter "e" is an integer of from 1 to 2.

15. The photochromic article of claim 14 wherein the photochromic compound is present in amounts of from 0.05 to 10 weight percent.

16. The photochromic article of claim 15 wherein the host material is selected from poly and copolymers polyol (allyl carbonate) and vinyl acetate.

17. The photochromic article of claim 16 wherein the copolymer is from 80-90 percent diethylene glycol bis(allyl carbonate) and 10-20 percent vinyl acetate.

18. The photochromic article of claim 14 wherein the host material is a polymer prepared from diethylene glycol bis(allyl carbonate).

19. The photochromic article of claim 18 wherein the article is a plano or ophthalmic lens.

20. The article of claim 14 wherein when e is 1, the substituent is located at the number 7 carbon atom position, and when e is 2, the substituents are located at the numbers 6 and 7 or 5 and 7 carbon atom positions.

21. 1',3'-Dihydrol-1',3',3'-trimethyl-5,7-dimethoxyspiro [2H-1,4-benzoxazine-2-2'-[2H-]pyrrolo[2,3-b-pyridine].

22. 1'3'-Dihydro-1',3'-dimethyl-3'-ethyl-5,7-dimethoxyspiro-[2H-1,4-benzoxazine-2-2'-[2H-]pyrrolo[2,3-b-pyridine].

23. 1',3'-Dihydro-1',3',3',6'-tetramethyl-5,7-dimethoxyspiro [2H-1,4-benzoxazine-2-2'-[2H-]pyrrolo[2,3-b-pyridine].

24. 1'340 -Dihydro-1',3',3'-trimethyl-5,6',7-trimethoxyspiro [2H-1,4-benzoxazine-2-2'-[2H-]pyrrolo[2,3-b-pyridine].

25. 1'3'-Dihydro-1',3',3'-trimethyl-5,7-dimethoxyspiro [2H-1,4-benzoxazine-2-2'-[2H-]pyrrolo[3,2,-c-pyridine].

26. 1'3'-Dihydro-1',3',3'-trimethyl-5,7-dimethoxyspiro [2H-1,4-benzoxazine-2-2'-[2H-]pyrrolo[3,2,-c-pyridine].

* * * * *

UNITED STATES PATENT AND TRADEMARK OFFICE
CERTIFICATE OF CORRECTION

PATENT NO. : 4,986,934

DATED : January 22, 1991

INVENTOR(S) : Patricia L. Kwiatkowski et al

It is certified that error appears in the above-identified patent and that said Letters Patent is hereby corrected as shown below:

Claim 5, column 18, line 26, "when is 2" should be -- when e is 2--.

Claim 10, column 19, line 18, "poly and" should be --poly[diethylene glycol bis(allyl carbonate)] and--.

Claim 16, column 20, line 37, "poly and" should be --poly[diethylene glycol bis(allyl carbonate)] and--.

Claim 21, column 20, line 51, "Dihydrol" should be --Dihydro--;

column 20, line 52, "[2,3-b-pyridine]" should be --[2,3-b-pyridine]--.

Claim 22, column 20, line 56, "[2,3-b-pyridine]" should be --[2,3-b-pyridine]--.

Claim 23, column 20, line 59, "[2,3-b-pyridine]" should be --[2,3-b-pyridine]--.

Claim 24, column 20, line 60, "1'340-Dihydro-" should be --1'3'-Dihydro--;

column 20, line 60, "[2,3-b-pyridine]" should be --[2,3-b-pyridine]--.

Claim 25, column 20, line 64, "[3,2,-c-pyridine] should be --[3,2-c-pyridine].

UNITED STATES PATENT AND TRADEMARK OFFICE
CERTIFICATE OF CORRECTION

PATENT NO. : 4,986,934
DATED : January 22, 1991
INVENTOR(S) : Patricia L. Kwiatkowski, et al.

It is certified that error appears in the above-identified patent and that said Letters Patent is hereby corrected as shown below:

Claim 26, column 20, line 67, "[3,2,-c-pyridine] should be [3,2,-b pyridine].

Signed and Sealed this

Twenty-seventh Day of October, 1992

Attest:

DOUGLAS B. COMER

Attesting Officer      Acting Commissioner of Patents and Trademarks